United States Patent [19]

Thoma et al.

[11] 4,028,362

[45] June 7, 1977

[54] PROCESS FOR THE PREPARATION OF QUINOLINES

[75] Inventors: Jozef A. Thoma, Sittard; Petrus A. M. J. Stijfs, Munstergeleen, both of Netherlands

[73] Assignee: Stamicarbon B. V., Geleen, Netherlands

[22] Filed: Dec. 12, 1974

[21] Appl. No.: 532,294

[30] Foreign Application Priority Data

Dec. 15, 1973 Netherlands .................... 7317228

[52] U.S. Cl. .................... 260/283 SY; 260/283 R
[51] Int. Cl.$^2$ .................... C07D 215/00
[58] Field of Search .................... 260/283 SY, 283 R

[56] References Cited

UNITED STATES PATENTS 3,007,931  11/1961  Simpson et al. ............. 260/283 SY

FOREIGN PATENTS OR APPLICATIONS 1,304,155  1/1973  United Kingdom ......... 260/283 SY Primary Examiner—Donald G. Daus
Assistant Examiner—Mary C. Vaughn
Attorney, Agent, or Firm—Cushman, Darby & Cushman

[57] ABSTRACT

In a process for treating 2-(beta-cyanoethyl)-cyclohexanones with a dehydrogenation catalyst to produce the corresponding quinolines, the improvement comprising passing the 2-(beta-cyanoethyl)-cyclohexanone over a dehydrogenation catalyst at temperatures below 230° C and thereafter contacting the resulting reaction product, in the gaseous state and in the presence of hydrogen, at a temperature of over 230° C.

4 Claims, No Drawings

PROCESS FOR THE PREPARATION OF QUINOLINES

The invention relates to a process for preparing a reaction mixture containing quinoline, and alkyl substituted quinolines, in which a 2-(beta-cyanoethyl)-cyclohexanone, or a substituted 2-beta-cyanoethyl-cyclohexanone, is brought into contact with a dehydrogenation catalyst in the gaseous phase in the presence of hydrogen.

A process for preparing quinolines is disclosed in British Patent Specification No. 1,304,155. According to this patent specification, a reaction mixture containing quinoline and hydroquinolines is obtained from 2-(beta-cyanoethyl)-cyclohexanone at a temperature of 250° C with a conversion of 100%. In this case the actual yield of quinoline and hydroquinolines is 96% of the theoretical yield. Such a conversion and yield are, practically, very desirable. It has been found, however, that the catalyst, in that prior art process will have to be reactivated after some time, e.g. 200–300 hours, because the conversion and yield will otherwise fall off considerably. Frequent activation of the catalyst renders such a process less practical for commercial purposes.

A process has now been found in which the catalyst can be used considerably longer without reduction in the conversion and yields of the basic process.

SUMMARY OF THE INVENTION

The process according to the invention is characterized in that the gaseous starting mixture of 2-(beta-cyanoethyl)-cyclohexanone, or 2-(beta-cyanoethyl)-substituted cyclohexanones, is first brought into contact with the catalyst at a temperature of below 230° C and the resulting reaction product is subsequently brought into contact with the catalyst in the gaseous state and in the presence of hydrogen at a temperature of over 230° C. By reaction products is meant quinolines, as well as hydroquinolines.

DETAILED DESCRIPTION OF THE INVENTION

The invention is directed to a process for contacting 2-(beta-cyanoethyl)-cyclohexanones with dehydrogenation catalysts to produce the corresponding quinolines. The process in accordance with the invention is a two-stage process comprising contacting a gaseous starting mixture of a 2-(beta-cyanoethyl)-cyclohexanone, or 2-(beta-cyanoethyl)-substituted-cyclohexan-1-ones, with a dehydrogenation catalyst at temperatures below 230° C and subsequently treating the resulting reaction product by contacting the resulting reaction product with the catalyst, in the gaseous state and in the presence of hydrogen at temperatures over 230° C. By this two-step heating process, the lifetime of the catalyst is lengthened, without concomitant reduction in conversion yields.

The first stage of the process, which requires treating 2-(beta-cyanoethyl)-cyclohexanones, at temperatures below 230° C, may be conducted at temperatures of 150° to 230° C. Preferably, the temperature of the first stages of the process is conducted between temperatures of 185° to 220° C. The second stage of the process which requires contacting the products of the first stage of the process at temperatures above 230° C may be conducted at temperatures between 230° and up to 400° C. Preferably, the temperature of the second stage of the process lies between 260° and 300° C. At preferred temperature ranges, the life of the dehydrogenation catalyst appears to be extremely long.

As set forth above, the gaseous starting material or reactant comprises vaporized 2-(beta-cyanoethyl)-cyclohexanones. Also the process is applicable to 2-(beta-cyanoethyl)-alkyl substituted cyclohexanones. Particularly, the reactants of the process are compounds of the general formula

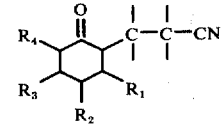

wherein each of $R_1$, $R_2$, $R_3$, and $R_4$ is the same or different, and is a hydrogen or an alkyl group of 1 to 4 carbon atoms. When alkyl substituted cyclohexanones are employed according to the process, the summation of the carbon atoms of $R_1$, $R_2$, $R_3$ and $R_4$ is no greater than 10. According to one aspect of the invention, each of $R_1$, $R_2$, $R_3$ and $R_4$ is hydrogen. Generally, the cyclo-hexanone may contain one or more alkyl groups in the 3, 4, 5 or 6 position of the cyclohexanone ring. A process for preparing these starting materials is disclosed in U.S. Pat. No. 2,850,519, which is hereby incorporated by reference.

As stated above, the 2-(beta-cyanoethyl)-cyclohexanone is in the gaseous state. The first stage of the process requires contacting the vaporized 2-(beta-cyanoethyl)-cyclohexanone with the dehydrogenation catalyst. Optionally, the vaporized 2-(beta-cyanoethyl)-cyclohexanone may be admixed with hydrogen gas for both steps of the process. In addition to hydrogen admixed with the gaseous starting material, the reactant mixture may contain nitrogen gas. The mole ratio of hydrogen to reactants may vary from 1,1 : 1 to 15 : 1. When nitrogen is present, the moles of hydrogen gas to moles of nitrogen gas may vary from 4 : 1 to 1 : 1.

Various known dehydrogenation catalysts may be used in the process of the invention. The catalyst in the first and the second stages of the process of the invention may be the same or different. Normally these catalysts are used on a carrier, such as e.g., silica gel, aluminum oxide, magnesium oxide, and mixtures of these materials. For example, platinum or aluminum oxide may be used, nickel on silica gel, palladium on aluminum oxide or copper on magnesium oxide. Examples of known suitable dehydrogenation catalysts, which may be used in the two-stage process of the invention, include metals or compounds of metals selected from the class consisting of group VIII and group I B of the periodic table 5, such as copper, silver, gold, iron, nickel, cobalt, platinum, palladium, ruthenium, rhodium, osmium, and iridium. The catalyst may be used as a fixed bed, a fluid bed, or in any other way. The catalyst of the invention may be regenerated by known processes.

The space velocity in each stage of the process of the invention may be varied, e.g. between 0.01 to 2 grams of starting cyanoketone per milliliter of catalyst mass per hour. The amount of hydrogen required in the gaseous mixture, may vary, as set forth above. The amount is usually so chosen that after each stage at least 0.1 mole of hydrogen per mole of original cyanoketone is present as such. However, larger amounts of hydrogen may be used without deleterious side effects. After termination of the reaction, the hydrogen present may be recovered and recycled.

The gaseous reaction mixture obtained in the first stage of the process according to the invention will contain various amounts of water, as a by-product of the process. Preferably, this water will be separated off, since the second stage of the reaction process may be undertaken in smaller apparatus, although under otherwise similar conditions.

The reaction mixture obtained according to the process of the invention contains not only quinoline, or alternatively alkyl substituted quinolines depending upon the 2-(beta-cyanoethyl)-cyclohexanone used, but also contains correspondingly unsubstituted or substituted hydroquinolines. After condensation of the resulting gaseous reaction mixture, the mixture of quinolines and hydroquinolines may be separated by distillation. If hydroquinolines are not desirable, the hydroquinolines separated off in the distillation may be recycled to the second stage of the process of the invention.

The quinolines may be used for medicinal purposes; preserving anatomical specimens, in the manufacture of the quinolinol sulfates, in the manufacture of niacin, in the manufacture of copper-8-quinolinolates and in the preparation of flavours and perfumes.

The process according to the invention will be further elucidated in the following examples.

EXAMPLE I

A gaseous mixture consisting of 2-($\beta$-cyanoethyl)-cyclohexanone and hydrogen, which was obtained by evaporating liquid 2-($\beta$-cyanoethyl)-cyclohexanone and mixing with hydrogen, was passed, for 1301 hours, from the top downwards through a vertical tubular reactor of 25 mm in diameter and 200 mm in length, which was provided with a catalyst bed and a heating jacket. The catalyst used was palladium on aluminum oxide (0.5 % by weight of palladium, bulk density 1.07 grams per milliliter), which was previously treated with hydrogen at 270° C.

The gaseous reaction mixture was subsequently passed through a collector cooled with ice, in which the reaction product condensed. After operating times of 6, 121, 385, 625, 889, 1153 and 1300 hours, the amount of 2-($\beta$-cyanoethyl)-cyclohexanone passed through and the amount of reaction product obtained were measured for 1 hour under constant conditions. The amount of 2-($\beta$-cyanoethyl)-cyclohexanone was determined by measuring the loss in weight of liquid 2-($\beta$-cyanoethyl)-cyclohexanone. The amount of reaction product obtained was determined by changing over from the collector to an empty collector cooled with ice and measuring the gain in weight. The collected reaction product was analyzed gas-chromatographically.

The results are compiled in Table 1.

Table 1

| Operating time, in hours | 6 | 121 | 385 | 625 | 889 | 1153 | 1300 |
|---|---|---|---|---|---|---|---|
| Temp. of gas mixture, in ° C, measured at 1 mm over catalyst bed | 200 | 200 | 203 | 207 | 207 | 207 | 207 |
| Highest temperature of catalyst bed, in ° C | 204 | 203 | 206 | 208 | 211 | 211 | 211 |
| Space velocity, in grams of 2-($\beta$cyanoethyl)-cyclohexanone per ml of catalyst per hour | 0,15 | 0,15 | 0,15 | 0,15 | 0,15 | 0,15 | 0,15 |
| Moles of hydrogen per mole of 2-($\beta$-cyanoethyl-cyclohexanone | 13,2 | 13,2 | 13,2 | 13,2 | 13,2 | 13,2 | 13,2 |
| Conversion, in % | 100 | 100 | 100 | 99,2 | 97,3 | 94,3 | 93 |
| Yield of quinoline, in % | 1 | 1 | 1,5 | 1,5 | 2 | 2 | 2 |
| Yield of decahydroquinoline, in % | 49 | 41 | 36 | 35 | 33 | 35 | 32 |
| Yield of 5,6,7,8-tetrahydroquinoline, in % | 41 | 45 | 50 | 50 | 51 | 51 | 51 |
| Yield of 1,2,3,4-tetrahydroquinoline, in % | 6 | 5,5 | 6 | 6 | 7 | 7 | 6 |
| Total yield | 97 | 92,5 | 93,5 | 92,5 | 93 | 95 | 91 |

Part of the resulting reaction mixture was evaporated, mixed with hydrogen and nitrogen, and passed over a catalyst bed consisting of palladium on aluminum oxide (0.5% by weight of palladium, bulk density 1.07 grams per milliliter) for 1130 hours. The amount of nitrogen was 2.56 moles per mole of gaseous reaction mixture and the amount of hydrogen 7.68 moles per mole of gaseous reaction mixture.

This gaseous starting mixture contained 1.5% by weight of 2-($\beta$-cyanoethyl)-cyclohexanone 5.4% by weight of 1,2,3,4-tetrahydroquinoline, 1.2% by weight of quinoline, 41.3% by weight of 5,6,7,8-tetrahydroquinoline, 38.5% by weight of decahydroquinoline, and 12% by weight of water.

The analyses and measurements were carried out in the same way as described in the first section of this example.

The results are compiled in Table 2.

Table 2

| Operating time, in hours | 25 | 168 | 336 | 504 | 768 | 937 | 1129 |
|---|---|---|---|---|---|---|---|
| Temperature of gas mixture in ° C, measured at 1 mm over catalyst bed | 271 | 285 | 285 | 294 | 294 | 304 | 304 |
| Highest temperature of catalyst bed, in ° C | 266 | 280 | 281 | 290 | 292 | 300 | 301 |
| Space velocity of the gas mixture, in grams per ml of catalyst per hour | 0,2 | 0,2 | 0,2 | 0,2 | 0,2 | 0,2 | 0,2 |
| Conversion, in % | 34,4 | 31,3 | 31,3 | 28,2 | 29,7 | 28,2 | 28,2 |
| Yield of quinoline relative to converted starting mixture, in % | 95 | 93 | 93 | 94 | 90 | 94 | 94 |

EXAMPLE II

In the same way as in example 1, a gaseous mixture of 2-($\beta$-cyanoethyl)-cyclohexanone and hydrogen, to which also an amount of nitrogen was added, was passed over a catalyst consisting of palladium on aluminum oxide (0.5% by weight of palladium, bulk density 1.07 grams per milliliter) for 1301 hours.

The amounts of hydrogen and nitrogen in the gaseous mixture were 15.6 moles and 5.2 moles, respectively, per mole of 2-($\beta$-cyanoethyl)-cyclohexanone. The pressure was 1.5 atm.

The results are compiled in Table 3.

After 1301 hours the catalyst was regenerated by treating it with air at a temperature of 200°–300° C for 20 hours. In the same way as in the first section of this example, a gas mixture of 2-(β-cyanoethyl)-cyclohexanone, hydrogen and nitrogen was then passed over this catalyst for 722 hours.

The amounts of hydrogen and nitrogen in the gaseous mixture were 15.6 moles and 5.2 moles, respectively, per mole of 2-(β-cyanoethyl)-cyclohexanone.

The pressure was 1.5 atm.

The results are compiled in Table 4.

| | Table 3 | | | Table 4 | | |
|---|---|---|---|---|---|---|
| Operating time, in hours | 6 | 385 | 889 | 1300 | 26 | 362 | 721 |
| Temperature of gas mixture, in ° C, measured at 1 mm over catalyst bed | 200 | 203 | 207 | 207 | 200 | 200 | 205 |
| Highest temperature of catalyst bed, in ° C | 204 | 206 | 211 | 211 | 204 | 203 | 209 |
| Space velocity of the gas mixture, in grams per ml of catalyst per hour | 0,15 | 0,15 | 0,15 | 0,15 | 0,15 | 0,15 | 0,15 |
| Conversion, in % | 100 | 99,9 | 97,1 | 93,6 | 100 | 99,8 | 97 |
| Yield of quinoline, in % | 0,6 | 0,7 | 1,3 | 1,3 | 0,8 | 0,7 | 1,0 |
| Yield of decahydroquinoline, in % | 56 | 45 | 38 | 36 | 52 | 43 | 34 |
| Yield of 5,6,7,8-tetrahydroquinoline, in % | 36 | 45 | 49 | 45 | 43 | 46 | 49 |
| Yield of 1,2,3,4-tetrahydroquinoline, in % | 4 | 5 | 6 | 6 | 4 | 4 | 4 |
| Total yield | 96,6 | 95,7 | 94,3 | 88,3 | 99,8 | 93,7 | 88 |

Part of the resulting reaction mixture was subjected to fractional distillation to remove water. The reaction mixture was then evaporated, mixed with 6.75 moles of hydrogen and 2.25 moles of nitrogen per mole of gaseous reaction mixture, and passed over a catalyst consisting of palladium on aluminum oxide (0.5% by weight of palladium, bulk density 1.07 grams per milliliter) for 2402 hours.

The gaseous reaction mixture used as the starting product contained 38.1% by weight of decahydroquinoline, 52% by weight of 5,6,7,8-tetrahydroquinoline, 5% by weight of 1,2,3,4-tetrahydroquinoline, and 3% by weight of quinoline.

The results are complied in Table 5.

Table 5

| Operating time, in hours | 6 | 386 | 725 | 1322 | 1562 | 2066 | 2401 |
|---|---|---|---|---|---|---|---|
| Temperature of gas mixture, in ° C, measured at 1 mm over catalyst bed | 264 | 277 | 283 | 293 | 293 | 293 | 293 |
| Highest temperature of catalyst bed, in ° C | 258 | 275 | 280 | 290 | 290 | 290 | 290 |
| Space velocity of gas mixture, in grams per ml of catalyst per hour | 0,2 | 0,2 | 0,2 | 0,2 | 0,2 | 0,2 | 0,2 |
| Conversion, in % | 37,8 | 30,4 | 32,4 | 34,4 | 34,2 | 32,8 | 33 |
| Yield of quinoline, relative to converted starting mixture | 94 | 98 | 96 | 99 | 99 | 98 | 98 |

COMPARATIVE EXAMPLE

In the same way as in example 1, a gaseous mixture of 2-(β-cyanoethyl)-cyclohexanone and hydrogen (10 moles of hydrogen per mole of 2-(β-cyanoethyl)-cyclohexanone) was passed over a catalyst consisting of palladium on aluminum oxide (0.5% by weight of palladium, bulk density 1.07 grams per milliliter) for 290 hours.

The results are compiled in Table 6, which shows that the conversion and the yield rapidly decrease.

After 290 hours the catalyst was regenerated by treating it with air at a temperature of 200°-300° C for 20 hours.

Subsequently, a mixture of 2-(β-cyanoethyl)-cyclohexanone and hydrogen (10 moles of hydrogen per mole of 2-(β-cyanoethyl)-cyclohexanone) was again passed over the regenerated catalyst for 71 hours.

The results are compiled in Table 7. It appears from these results that the regeneration of the catalyst has only a moderate effect and the conversion and the yield likewise decrease very rapidly.

| | Table 6 | | | Table 7 | | |
|---|---|---|---|---|---|---|
| Operating time, in hours | 101 | 215 | 289 | 4 | 28 | 70 |
| Temperature of gas mixture, in ° C, measured at 1 mm over catalyst bed | 252 | 260 | 272 | 252 | 252 | 252 |
| Highest temperature of catalyst bed, in ° C | — | — | — | — | — | — |
| Space velocity of gas mixture, in grams per ml of catalyst per hour | 0,1 | 0,1 | 0,1 | 0,1 | 0,1 | 0,1 |
| Conversion, in % | 93,5 | 74 | 57 | 100 | 90 | 73 |
| Yield of quinoline, in % | 36 | 26 | 21 | 54 | 30 | 20 |
| Yield of 5,6,7,8-tetrahydroquinoline, in % | 33 | 33 | 30 | 24 | 40 | 43 |
| Yield of 1,2,3,4-tetrahydroquinoline, in % | 4 | 2 | 1 | 5 | 4 | 2 |
| Total yield | 73 | 61 | 52 | 83 | 74 | 65 |

The results set forth in Table I, represent results undertaken according to the process conditions of the first stage of the process of the invention. It will be noted that conversion proceeds in excellent yields for up to 1300 hours. The total yield of products resulting from the conversion are also excellent.

Table 2 represents results obtained by passing the gaseous starting mixture of the first stage of the process of the invention over a dehydrogenation catalyst at temperatures within the ranges of the second stage of the process in accordance with the invention. It will be noted that the percent of conversion of products obtained from the first stage of the process in accordance with the invention remains steady for up to 1129 hours. It will also be noted that conversion in the second stage of the process results in very good yields of quinoline for extended periods of time, up to 1129 hours.

Table 3 and Table 4 represent results obtained by employing the same catalysts, which has been regenerated, for two different consecutive runs of the first stage of the process. Table 3 represents the results with respect to the percent conversion and total yield products produced in accordance with the first stage of the process of the invention. In Table 3, the dehydrogenating catalyst was effective for up to 1300 hours. The results of Table 4 are based on regenerating the catalyst used in Table 3 and then using that catalyst again with fresh 2-(beta-cyanoethyl)-cyclohexanone to undertake the first stage of the reaction process with the same catalyst. The results of Table 4 indicate that percent conversion and total yields will remain constant, even on reuse of the catalyst.

Table 5 represents results concerning the second stage of the process of the invention. Reaction products obtained from the first stage of the process of the invention, as in Table 3 and in Table 4. These results are comparable to those set forth in Table 2 (an experiment dealing with the second stage of the process of the invention). As can be noted, conversion and percent yields of quinoline remain constant up to 2400 hours.

Table 6 and Table 7 represent results when a process of treating 2-(beta-cyanoethyl)-cyclohexanone with a dehydrogenation catalyst at prior art temperatures. As will be noted in Table 6, percent conversion and total yield decrease with time.

Table 7 represents results obtained by reducing the catalyst employed in the experiments set forth in Table 6 after the catalyst has been regenerated. The experiments in Table 7 were undertaken at temperatures outside the scope of the invention claimed. The results of Table 7 are consistent with the results of Table 6, in that undertaking the dehydrogenation of 2-(beta-cyanoethyl)-cyclohexanone in one step, at high temperatures, results in percent conversion and total yield decreases with time. Such results reflect deactivation of the catalyst used.

What is claimed is:

1. A process for preparing quinolines, consisting essentially of contacting a vaporized compound of the formula

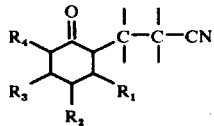

wherein each of $R_1$, $R_2$, $R_3$ and $R_4$ is the same or different and is a hydrogen atom or an alkyl group of 1 to 4 carbon atoms, wherein the summation of carbon atoms of the groups $R_1$, $R_2$, $R_3$ and $R_4$ is no greater than 10, at elevated temperatures with a dehydrogenation catalyst in the presence of hydrogen in two stages, wherein in a first stage (1) said vaporized compound is contacted with a dehydrogenation catalyst at a temperature ranging between 185° to 220° C to form a vaporized mixture of products and in a second stage (2) said mixture is contacted with the catalyst in the presence of hydrogen at a higher temperature than that of stage (1) and being between 260° and 300° C, wherein the mixture of products includes water, and wherein said water is removed prior to undertaking step (2).

2. A process for preparing quinolines, consisting essentially of contacting a vaporized compound of the formula

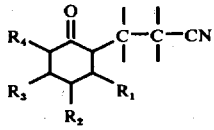

wherein each of $R_1$, $R_2$, $R_3$ and $R_4$ is the same or different and is a hydrogen atom or an alkyl group of 1 to 4 carbon atoms, wherein the summation of carbon atoms of the groups $R_1$, $R_2$, $R_3$ and $R_4$ is no greater than 10, at elevated temperatures with a dehydrogenation catalyst in the presence of hydrogen in two stages, wherein in a first stage (1) said vaporized compound is contacted with a dehydrogenation catalyst at a temperature ranging between 180° to 220° C to form a vaporized mixture of products and in a second stage (2) said mixture is contacted with the catalyst in the presence of hydrogen at a higher temperature than that of stage (1) and being between 260° C and 300° C, wherein hydroquinolines are produced, wherein said hydroquinolines are separated from the resulting reaction mixture and recycled to step (2).

3. In a process for preparing quinolines, by contacting a vaporized compound of the formula

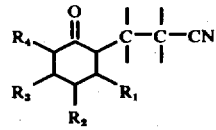

wherein each $R_1$, $R_2$, $R_3$ and $R_4$ is the same or different and is hydrogen or alkyl groups of 1 to 4 carbon atoms, and wherein the summation of the carbon atoms of $R_1$, $R_2$, $R_3$ and $R_4$ is no greater than 10, with a dehydrogenation catalyst in the presence of hydrogen, the improvement consisting essentially of a two-stage process including a first stage (1) of contacting said vaporized compound with a dehydrogenation catalyst at a temperature of 185° to 220° C to form a vaporized mixture of products and a second stage (2) of contacting said mixture with the catalyst in the presence of hydrogen at temperatures over 260° C and up to 300° C, wherein said mixture of products contains water, and wherein said water is separated from the mixture prior to subjecting the mixture to the process of step (2).

4. In a process for preparing quinolines, by contacting a vaporized compound of the formula

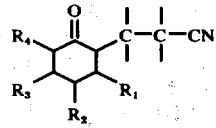

wherein said $R_1$, $R_2$, $R_3$ and $R_4$ is the same or different and is hydrogen or alkyl groups of 1 to 4 carbon atoms, and wherein the summation of the carbon atoms of $R_1$, $R_2$, $R_3$ and $R_4$ is no greater than 10, with a dehydrogenation catalyst in the presence of hydrogen, the improvement consisting essentially of a two-stage process including a first stage (1) of contacting said vaporized compound with a dehydrogenation catalyst at a temperature of 185° to 220° C to form a vaporized mixture of products and a second stage (2) of contacting said mixture with the catalyst in the presence of hydrogen at temperatures over 260° C and up to 300° C, wherein hydroquinolines are produced, and wherein said hydroquinolines are separated from quinolines produced by the process, and wherein said hydroquinolines are recycled to step (2).

* * * * *